(12) United States Patent
Chu et al.

(10) Patent No.: US 8,940,153 B2
(45) Date of Patent: *Jan. 27, 2015

(54) TEST SENSOR REAGENT HAVING CELLULOSE POLYMERS

(75) Inventors: Amy H. Chu, Elkhart, IN (US); Andrew J. Edelbrock, Granger, IN (US); Hope G. Spradlin, Granger, IN (US)

(73) Assignee: Bayer Healthcare LLC, Whippany, NJ (US)

( * ) Notice: Subject to any disclaimer, the term of this patent is extended or adjusted under 35 U.S.C. 154(b) by 702 days.

This patent is subject to a terminal disclaimer.

(21) Appl. No.: 12/083,952

(22) PCT Filed: Nov. 13, 2006

(86) PCT No.: PCT/US2006/043918
§ 371 (c)(1),
(2), (4) Date: Apr. 22, 2008

(87) PCT Pub. No.: WO2007/058999
PCT Pub. Date: May 24, 2007

(65) Prior Publication Data
US 2009/0152128 A1  Jun. 18, 2009

Related U.S. Application Data

(60) Provisional application No. 60/736,537, filed on Nov. 14, 2005.

(51) Int. Cl.
*C12Q 1/26* (2006.01)
*G01N 33/50* (2006.01)
*C12Q 1/00* (2006.01)

(52) U.S. Cl.
CPC ..................................... *C12Q 1/006* (2013.01)
USPC .............. 205/777.5; 204/403.04; 204/403.14

(58) Field of Classification Search
USPC ............. 204/403.01–403.15; 205/777.5, 778, 205/792; 435/200
See application file for complete search history.

(56) References Cited

U.S. PATENT DOCUMENTS

| | | | |
|---|---|---|---|
| 5,682,884 A | 11/1997 | Hill et al. | 128/637 |
| 5,708,247 A | 1/1998 | McAleer et al. | 204/403 |
| 5,709,837 A | 1/1998 | Mori et al. | 422/56 |
| 6,241,862 B1 | 6/2001 | McAleer et al. | 204/403 |

(Continued)

FOREIGN PATENT DOCUMENTS

| | | |
|---|---|---|
| DE | 10 2004 003793 A1 | 8/2005 |
| DE | 10 2004 003 793 A1 | 11/2005 |

(Continued)

OTHER PUBLICATIONS

Zen, Jyh-Myng, and Chin-Wen Lo. "A Glucose Sensor Made of an Enzymatic Clay-Modified Electrode and Methyl Viologen Mediator." Analytical Chemistry 68.15 (1996): 2635-640.*

(Continued)

*Primary Examiner* — Keith Hendricks
*Assistant Examiner* — Kourtney S Carlson
(74) *Attorney, Agent, or Firm* — Nixon Peabody LLP

(57) ABSTRACT

A test sensor reagent for measuring the concentration of analytes in body fluids includes cellulose polymers for improving the stability of the test sensor and reducing the total assay time. The test sensor reagent also includes an enzyme, an electron transfer mediator and a rheological additive.

15 Claims, 8 Drawing Sheets

(56) References Cited

U.S. PATENT DOCUMENTS

| | | | |
|---|---|---|---|
| 6,270,637 B1 | 8/2001 | Crismore et al. | 204/403 |
| 6,531,040 B2 | 3/2003 | Musho et al. | 204/401 |
| 6,656,702 B1 | 12/2003 | Yugawa et al. | 435/26 |
| 6,982,027 B2 * | 1/2006 | Yagi | 204/403.06 |
| 2002/0189941 A1 * | 12/2002 | Katsuki et al. | 204/403.01 |
| 2003/0089730 A1 | 5/2003 | May et al. | 221/232 |
| 2003/0217918 A1 * | 11/2003 | Davies et al. | 204/403.02 |
| 2004/0005716 A9 | 1/2004 | Beaty et al. | 436/149 |
| 2004/0256248 A1 | 12/2004 | Burke et al. | 205/792 |
| 2004/0259180 A1 | 12/2004 | Burke et al. | 435/14 |
| 2004/0260511 A1 | 12/2004 | Burke et al. | 702/182 |
| 2005/0013731 A1 | 1/2005 | Burke et al. | 422/56 |
| 2005/0016844 A1 | 1/2005 | Burke et al. | 204/403.01 |
| 2005/0023137 A1 | 2/2005 | Bhullar et al. | 204/403.1 |
| 2008/0199937 A1 * | 8/2008 | Chu et al. | 435/200 |
| 2009/0123955 A1 * | 5/2009 | Marfurt | 435/10 |

FOREIGN PATENT DOCUMENTS

| | | | |
|---|---|---|---|
| EP | 0 524 596 B1 | 1/1993 | |
| EP | 0 525 550 B1 | 2/1993 | |
| EP | 0 708 335 B1 | 4/1996 | |
| JP | 1991-296655 | 12/1991 | G01N 27/327 |
| JP | 09-318588 | 12/1997 | G01N 27/327 |
| JP | 2004-264247 | 9/2004 | G01N 27/327 |
| JP | 2005-043280 | 2/2005 | G01N 27/327 |
| JP | 2005-062027 | 3/2005 | C12Q 1/00 |
| WO | WO 00/42422 | 7/2000 | G01N 27/27 |
| WO | WO 2004/113900 A2 | 12/2004 | G01N 27/30 |
| WO | WO 2004/113901 A1 | 12/2004 | G01N 27/30 |
| WO | WO 2004/113902 A1 | 12/2004 | G01N 27/30 |
| WO | WO 2005/066356 A1 | 7/2005 | C12Q 1/00 |

OTHER PUBLICATIONS

Dow Corning Product Data Sheet for DC 1500 Dow Corning Antifoam, Dec. 21, 2009.*

Written Opinion corresponding to International Patent Application Serial No. PCT/US2006/043918, European Patent Office, dated Apr. 18, 2007; 9 pages.

International Search Report corresponding to International Patent Application Serial No. PCT/US2006/043918, European Patent Office, dated Apr. 18, 2007; 5 pages.

Burcak Alp, et al., "Glow-discharge-treated cellulose acetate (CA) membrane for a high linearity single-layer glucose electrode in the food industry", Elsevier, Food Research International, 33, (2000), pp. 107-112.

* cited by examiner

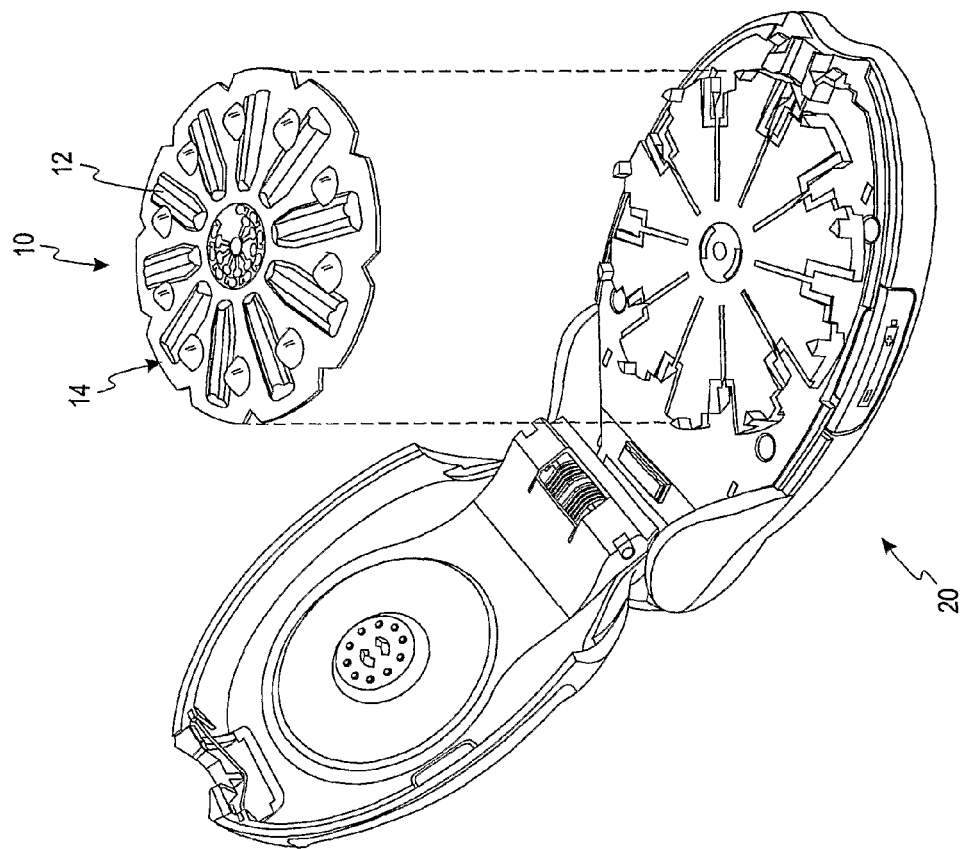

TEST SENSOR REAGENT HAVING CELLULOSE POLYMERS

CROSS-REFERENCE TO RELATED APPLICATIONS

This application claims priority to Application Ser. No. 60/736,537 filed on Nov. 14, 2005, which is incorporated by reference in its entirety.

FIELD OF THE INVENTION

The present invention relates generally to reagents used in test sensors and, more particularly, to reagents having cellulose polymers for improving test sensor stability and reducing total assay time.

BACKGROUND OF THE INVENTION

The quantitative determination of analytes in body fluids is of great importance in the diagnoses and maintenance of certain physiological abnormalities. For example, lactate, cholesterol and bilirubin should be monitored in certain individuals. In particular, determining glucose in body fluids is important to diabetic individuals who must frequently check the glucose level in their body fluids to regulate the glucose intake in their diets. The results of such tests can be used to determine what, if any, insulin or other medication needs to be administered. In one type of blood glucose testing system, test sensors are used to test a fluid such as a sample of blood.

A test sensor contains biosensing or reagent material that will react with the analyte of interest, such as blood glucose. The testing end of the test sensor is adapted to be placed into the fluid being tested, for example, blood that has accumulated on a person's finger after the finger has been pricked. The fluid is drawn into a capillary channel that extends in the test sensor from the testing end to the reagent material by capillary action so that a sufficient amount of fluid to be tested is drawn into the test sensor. In some test sensors, the fluid then chemically reacts with the reagent material in the test sensor resulting in an electrical signal indicative of the glucose level in the fluid being tested.

One problem with current test sensors is that the reagents may contain components that interfere with sensor stability. In particular, some components, such as polyethylene oxide ("PEO"), may be incompatible with other components, such as the enzyme and the electron transfer mediator, which are important for test sensors. Test sensors having reagents that are formulated with components that are, for example, incompatible with the enzyme and the electron transfer mediator may exhibit poor test sensor stability over time. This instability is especially apparent when the total assay time is less than about 35 seconds. Thus, it would be desirable to have a test sensor reagent having components that improve test sensor stability.

SUMMARY OF THE INVENTION

According to one embodiment of the invention, a test sensor reagent composition is adapted to assist in determining an analyte concentration of a fluid sample. The reagent comprises an enzyme, an electron transfer mediator, a cellulose polymer and a rheological additive.

According to another embodiment of the invention, a method of determining an analyte concentration of a fluid sample comprises the acts of providing an electrochemical test sensor that is adapted to assist in determining the analyte concentration. The electrochemical test sensor comprises a plurality of electrodes including a counter electrode and a working electrode, a fluid receiving area, and a test sensor reagent including a cellulose polymer. The method also includes the acts of determining the analyte concentration in an assay time of less than about 35 seconds.

According to another embodiment of the invention, a method of determining an analyte concentration of a fluid sample comprises the acts of pricking a finger of a test subject to produce the fluid sample, placing the fluid sample having at least one analyte within a test sensor, contacting the fluid sample with a reagent comprising a cellulose polymer which assists in stabilizing the test sensor, providing an electrical signal indicative of the analyte in the fluid sample, and determining the analyte using the electrical signal.

According to another embodiment of the invention, a cartridge for use in a test sensor comprises a plurality of test sensors and a housing adapted to store the plurality of test sensors. Each test sensor includes a reagent comprising a cellulose polymer that is adapted to stabilize the test sensor and reduce a total assay time to less than about 35 seconds.

According to another embodiment of the invention, a method of determining an analyte concentration of a fluid sample comprises the acts of pricking a finger of a test subject to produce the fluid sample, placing the fluid sample having at least one analyte within a test sensor, contacting the fluid sample with a reagent comprising a cellulose polymer which assists in stabilizing the test sensor and determining the analyte concentration of the fluid sample.

According to a further embodiment of the invention, a method of screen printing on a substrate comprises the acts of providing a screen that includes a first portion with a photosensitive emulsion and a second portion formed in the absence of a photosensitive emulsion, supplying a reagent comprising a solvent, a cellulose polymer and an enzyme to assist in determining an analyte concentration of a fluid sample on the screen, and contacting the reagent onto the substrate via the second portion of the screen.

The above summary of the present invention is not intended to represent each embodiment, or every aspect, of the present invention. Additional features and benefits of the present invention will become apparent from the detailed description, figures, and claims set forth below.

BRIEF DESCRIPTION OF THE DRAWINGS

FIG. 1 is a perspective view of a test sensor-dispensing instrument in the open position showing a sensor pack being inserted according to one embodiment.

FIG. 2b is a front view of a sensor-dispensing instrument according to one embodiment that is adapted to receive the cartridge of FIG. 2a.

DESCRIPTION OF ILLUSTRATED EMBODIMENTS

The present invention is directed to a reagent to be used in a single sensor instrument or a sensor-dispensing instrument that contains a plurality of electrochemical or optical test sensors. The electrochemical or optical test sensors are used to determine concentrations of at least one analyte in a fluid. Analytes that may be determined using the reagent of the present invention include glucose, lipid profiles (e.g., cholesterol, triglycerides, LDL and HDL), hemoglobin $A_{1C}$, fructose, lactate, or bilirubin. The present invention is not limited, however, to determining these specific analytes and it is contemplated that other analyte concentrations may be determined. The analytes may be in, for example, a whole blood sample, a blood serum sample, a blood plasma sample, or other body fluids like ISF (interstitial fluid) and urine.

The plurality of test sensors is typically stored in a disposable cartridge or container. In one embodiment, the plurality of test sensors may be stored in a sensor pack where the test sensors are individually packaged in sensor cavities (e.g., a blister-type pack). An example of a disposable cartridge 10 being placed in a sensor-dispensing instrument 20 is depicted in FIG. 1. The disposable cartridge 10 is an example of a blister-type pack. The cartridge 10 includes a plurality of test sensors 12 that are individually stored in a respective one of sensor cavities 14. It is contemplated that other sensor packs that individually hold the sensors may also be used.

Figure 2A:
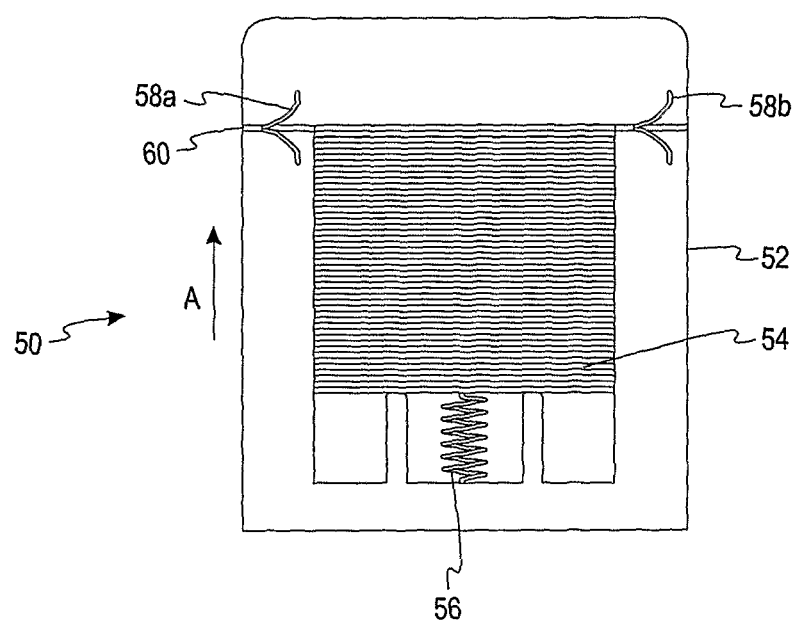
FIG. 2a is a front view of a disposable cartridge with a plurality of stacked test sensors according to one embodiment.
Figure 2B:
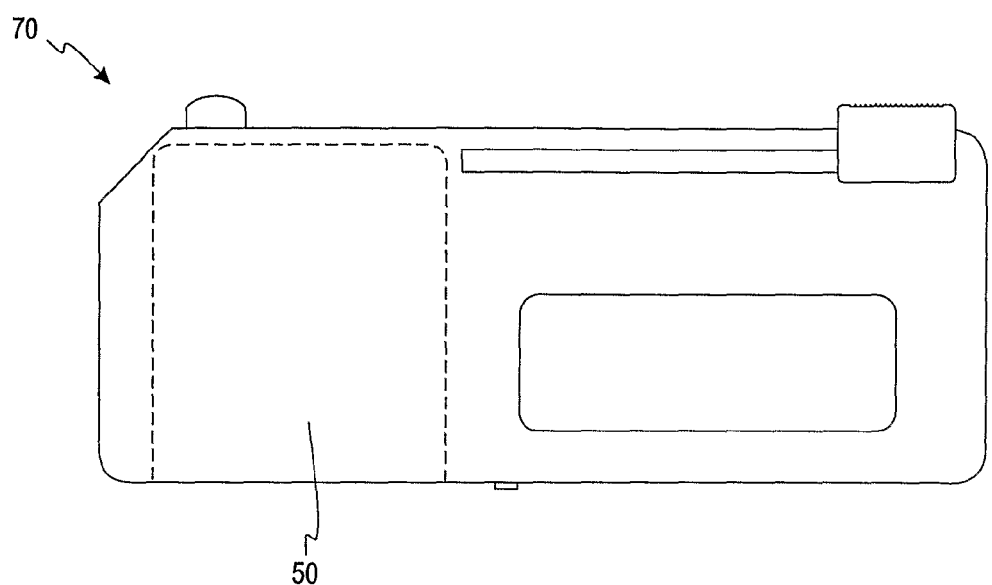

In an alternative embodiment, the plurality of test sensors may be stacked in a disposable cartridge such as shown in FIG. 2a. Referring to FIG. 2a, a disposable cartridge 50 includes a housing 52 and a plurality of stacked test sensors 54 that are moved in the direction of arrow A via a spring 56. The cartridge 50 also includes a plurality of seals 58a,b that protects the stacked test sensors 54 from humidity. The test sensors 54, one at a time, exit the cartridge 50, via opening 60. The disposable cartridge 50 may be stored in a sensor-dispensing instrument 70 of FIG. 2b. It is contemplated that other cartridges besides cartridges 10, 50 may be used with the present invention.

The cartridges 10, 50 of FIGS. 1 and 2a or a container of single test sensors may vary in the number of test sensors that are included so as to address the needs of different users. Typically, the cartridges or containers contain from about 10 to about 100 test sensors and, more specifically, contain from about 25 to about 50 test sensors. Because of limited shelf- and use-life of the test sensors, it is envisioned that a user who tests infrequently would likely desire a cartridge or container having less test sensors as opposed to a user who tests more frequently.

In some embodiments, the test sensors to be used in the cartridges or containers are typically provided with a capillary channel that extends from the front or testing end of the test sensor to the biosensing or reagent material disposed in the test sensor. When the testing end of the test sensor is placed into fluid (e.g., blood that is accumulated on a person's finger after the finger has been pricked), a portion of the fluid is drawn into the capillary channel by capillary action. The fluid then chemically reacts with the reagent in the test sensor so that an electrical signal indicative of the analyte (e.g., glucose) level in the fluid being tested is supplied and subsequently transmitted to an electrical assembly.

In some test sensors, the reagent is applied to a substrate via a screen printing process. The screen printing process allows a thin layer of the reagent to be applied to a small, flat test sensor, such as the test sensor shown in FIG. 4. This process uses a screen typically made with either a stretched stainless steel or polyester mesh and a photosensitive emulsion coating that is exposed in the desired pattern. The reagent ink is typically applied to the screen and a squeegee blade is used to force the reagent through the screen in the desired pattern. The desired pattern may include one portion of the screen having the photosensitive emulsion and another portion of the screen having no photosensitive emulsion. In one embodiment, the portion of the screen without the photosensitive emulsion may be contacted with the reagent ink.

The composition of the reagent that is applied to the test sensor may influence such items as the length of time needed to perform the testing to determine the analyte concentration (i.e., the assay time), the stability of the test sensor and the ease of the application of the reagent via the screen printing process. The composition of the reagent of the present invention includes ingredients that provide desirable test sensor characteristics, such as increased stability of the test sensor, reduced total assay time and improved adherence of the reagent to the substrate.

One embodiment of the present invention that provides such desirable characteristics includes a reagent having cellulose polymers. The cellulose polymers serve as a binder for the components of the reagent layer and help to increase the viscosity of the reagent. It has also been found that the use of cellulose polymers in the reagent improves the stability of the test sensor. A particularly desirable cellulose polymer includes hydroxyethyl cellulose ("HEC") polymer. HEC is desirable due to its stabilizing properties. Specifically, when HEC is used in place of other polymer materials, the degradation of glucose oxidase is reduced, as well as the occurrence of the reduction of the mediator. The reduction in these reactions leads to improved test sensor stability by reducing the background current of the test sensor. Other suitable polymers that may be used in the reagent formulation include carboxymethyl cellulose, cellulose acetate, ethylcellulose, or hydroxypropyl methylcellulose, polyvinyl pyrrolidone, polyvinyl alcohol, or combinations thereof.

According to one embodiment of the present invention, the reagent generally comprises about 1 wt. % to about 10 wt. % cellulose polymers of molecular weights between about 25,000 and about 2,000,000, and desirably from about 3 wt. % to about 6 wt. % cellulose polymers of molecular weights between about 300,000 to about 1,000,000. Cellulose polymers are commercially available from various suppliers. For example, Natrasol®, an HEC polymer, is available from Hercules Inc. in Wilmington, Del.

According to another embodiment of the present invention, in addition to the cellulose polymers described above, the reagent includes additional components such as an enzyme, an electron transfer mediator and Theological additives.

For testing blood glucose levels, a glucose oxidase enzyme may be used. Glucose oxidase enzyme reacts with glucose in the blood sample and produces an electrical signal that indicates the glucose concentration. The enzyme activities may be measured in terms of the activity unit (U) which is defined as the amount of enzyme that will catalyze the transformation of one micromole of a substrate per minute under standard conditions. The reagent may comprise about 0.5 wt. % up to about 5 wt. % glucose oxidase enzyme, and desirably from about 1.0 wt. % up to about 4.0 wt. %.

Glucose oxidase enzyme can be obtained commercially from companies such as Biozyme Laboratories International Ltd. in San Diego, Calif., Genzyme Corporation in Cambridge, Mass. and Amano Enzyme Inc. in Elgin, Ill. Depending on the analyte being tested, the reagent may contain other enzymes, such as glucose dehydrogenase, cholesterol oxidase, cholesterol dehydrogenase, lactate oxidase, etc., to detect other analytes in the blood sample in addition to glucose.

As described above, the reagent may also include an electron transfer mediator. Examples of mediators that may be used with the present invention include potassium ferricyanide, potassium ferrocyanide, ferrocene or its derivatives, quinone or its derivatives, organic conducting salts or viologen, in addition to other mediators. Preferably, the electron transfer mediator is a mixed-valence compound capable of forming redox couples. Depending on the electron transfer mediator that is used, the reagent generally comprises from about 1 wt. % to about 20 wt. % electron transfer mediator, and desirably from about 15 wt. % to about 20 wt. % electron transfer mediator. In one embodiment of the present invention, the electron transfer mediator is a ferricyanide mediator. Ferricyanide mediators, as well as other electron transfer mediators, are commercially available from various suppliers such as Sigma-Aldrich Co. It is contemplated that other electron transfer mediators, in addition to ferricyanide mediators, may be used in the present invention.

Rheological additives that are included in the reagent may include smectite clays such as montmorillonite, hectorite or bentonite clays or other suitable natural or synthetic materials. Hectorite is composed of clay minerals and is commercially available as Bentone® from Elementis Specialities Inc. in Hightstown, N.J. or as OPTIGEL® SH Synthetic Hectorite which is commercially available from Sud-Chemie Inc. in Louisville, Ky. Other rheological additives that may be used with the present invention may include other beneficiated clays, xanthum gum, fumed silica and Acti-Gel™ 208, a magnesium alumino silicate which is commercially available from Active Minerals Company LLC.

The rheological additives that may be used in the reagent of the present invention are desirably thixotropic or viscosity-modifying materials. Such materials improve the screen printing properties of the reagent. Specifically, the thixotropic additives of the present invention include materials that exhibit a decrease in viscosity over time. Additionally, the viscosity of the thixotropic additives of the present invention also decreases the longer the additives undergo shear. The rheological additives in the reagent may also serve as binder or filler materials.

In one embodiment, the reagent may comprise about 0.1 wt. % to about 3 wt. % smectite clay or other suitable rheological additive, and desirably from about 0.2 wt. % to about 1.6 wt. %. It is contemplated that other rheological additives having the properties described above may be used in the reagent. The amount and type of rheological additive that is used may vary depending on the polymer that is used in the reagent, as well as whether the reagent is aqueous- or organic-based.

In yet other embodiments of the present invention, the reagent may include additional components, such as a buffer and a wetting agent. Examples of buffers that may be used include citric acid, sodium citrate and other suitable buffers, such as phosphate buffers. The reagent may comprise about 10 mMolar to about 500 mMolar of the buffer and desirably from about 25 mMolar to about 200 mMolar. Other suitable buffers may include sodium acetate, Hepes buffer, etc. The buffer that is used in the reagent may be selected based on the electron transfer mediator that is used. For example, if a ferricyanide mediator is included in the reagent, a buffer that will maintain a lower pH level and that will not react with the ferricyanide mediator is desirable.

Suitable wetting agents may include fluorocarbon- or hydrocarbon-based surfactants. Some examples of surfactants that may be used with the present invention include Triton™ surfactants from The Dow Chemical Company in Midland, Mich. and Surfynol® additives from Air Products and Chemicals, Inc. in Allentown, Pa. The reagent may comprise about 0.01 wt. % to about 0.3 wt. % of a fluorocarbon-based surfactant, and desirably from about 0.02 wt. % to about 0.06 wt. %. Additionally, or alternatively, the reagent may comprise about 0.1 wt. % to about 5.0 wt. % of a hydrocarbon-based surfactant, and desirably from about 1.0 wt. % to about 3.0 wt. %.

The remainder of the formulation may contain water or other suitable solvents which may vary depending on the enzyme and electron transfer mediator chosen. The solvent should be inert to the enzyme and the electron transfer mediator.

Figure 3:
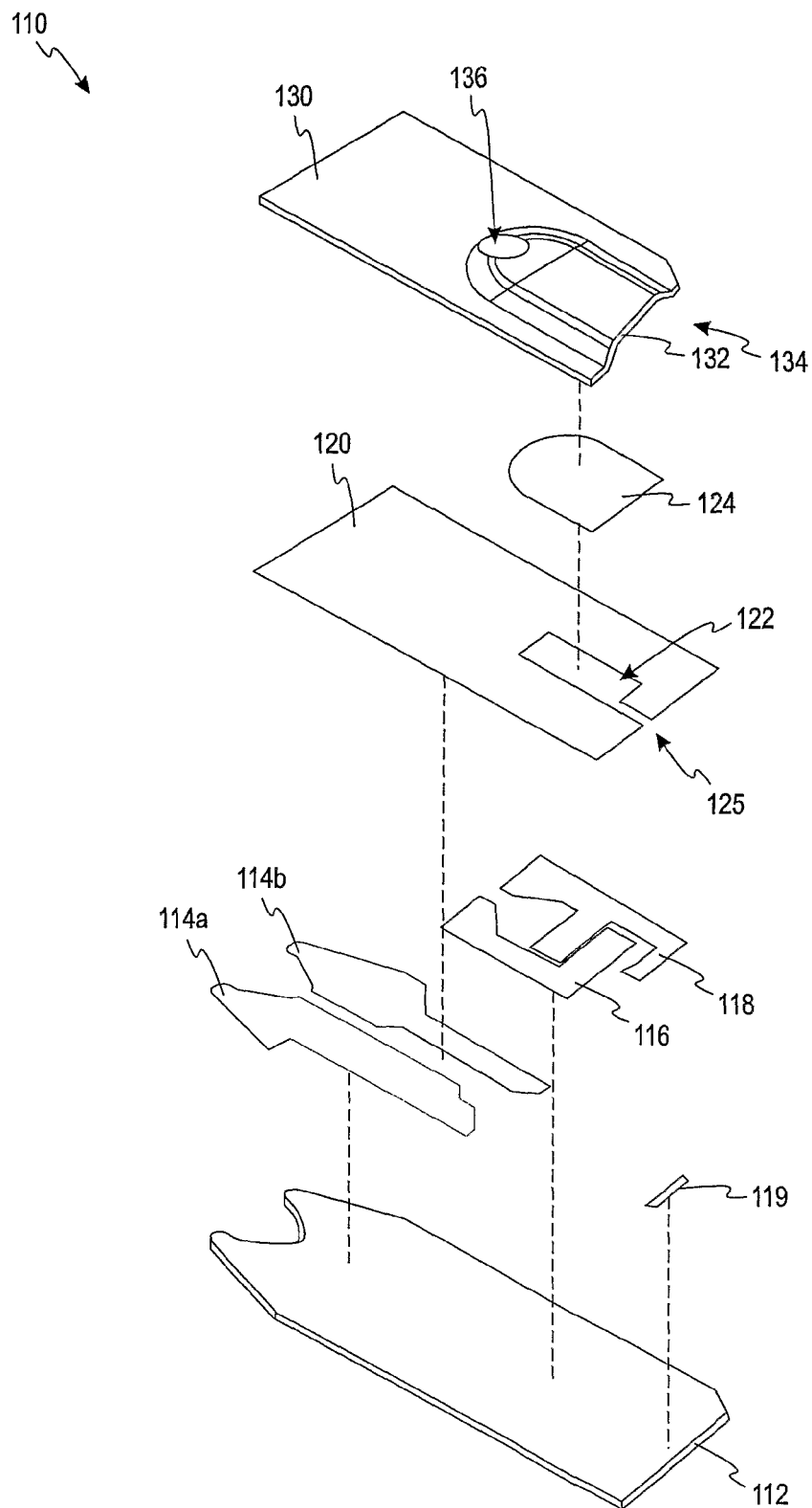
FIG. 3 is an exploded view of the components of a test sensor according to another embodiment.
Figure 4:
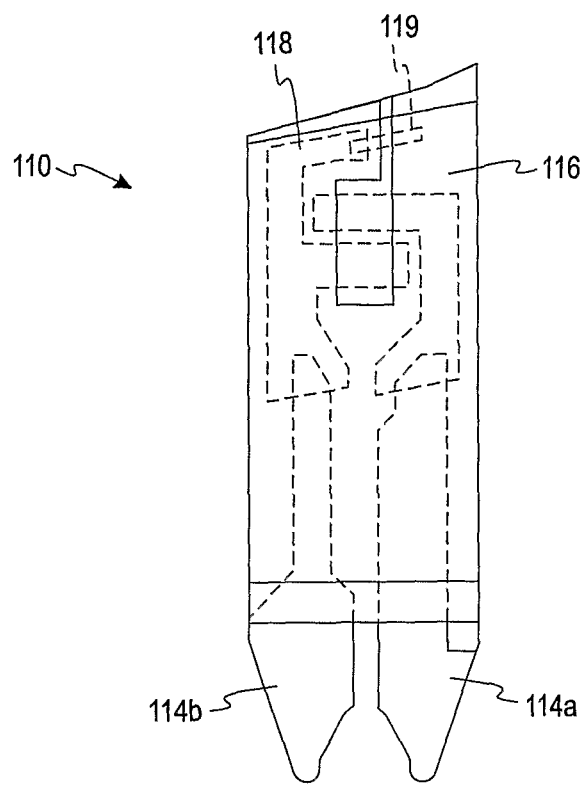
FIG. 4 is a front view of the electrochemical test sensor of FIG. 3.

FIGS. 3 and 4 depict another embodiment of the test sensor that is adapted to use the reagent described above. FIG. 3 is an exploded view of an electrochemical test sensor. The test sensor 110 comprises an insulating base 112 upon which is printed in sequence (typically by screen printing techniques) an electrical conductor pattern including first and second leads 114a, 114b (low resistance contacts), an electrode pattern including a working electrode 116, a counter electrode 118, an insulating (dielectric) layer 120 including an opening 122 and a channel 125, and a reaction layer 124.

The reaction layer 124 includes the reagent that converts the analyte of interest (e.g., glucose) into a chemical species that is electrochemically measurable, in terms of the electrical current it produces, by the components of the electrode pattern 116, 118. The reaction layer 124 is disposed over the opening 122 and channel 125 in the insulating layer 120. Thus, the portion of the reaction layer 124 exposed to the electrode pattern 116,118 is defined by the opening 122 and the channel 125 in the insulating layer 120. The working electrode 116 is electrically coupled to the first lead 114a, and the counter electrode 118 is electrically coupled to the second lead 114b. A trigger counter electrode subunit 119 is electrically coupled to the counter electrode 118 and serves as an underfill detection electrode in a two electrode system.

The test sensor 110 includes a lid 130 having a concave portion 132 that forms a capillary channel when mated with the insulating layer 120 for moving the liquid sample from an inlet 134 into the test sensor 110. The downstream end of the capillary channel includes one or more openings 136 for venting the capillary channel—the fluid sample flows from the inlet 134 into the test sensor 110 toward the opening 136. In use, the test sensor 110 collects a fluid sample (e.g., a blood sample from a patient's finger) by bringing the capillary channel inlet 134 into contact with the fluid sample.

The reagent of the present invention described herein may be used in a variety of test sensors. Some example of test sensors that may use the reagent formulation are the Ascensia™ Autodisc™ and Glucodisc Blood Glucose Test Strips that are designed to be used by the Ascensia™ BREEZE™ Blood Glucose Meter and the Ascensia™ DEX® 2/DEX® Blood Glucose Meter from Bayer Healthcare LLC of Tarrytown, N.Y.

As mentioned above, test sensor stability is improved by using reagents having cellulose-based polymers. This is particularly true for assay tests less than about 35 seconds, and especially desirable for assay tests less than about 25 seconds.

The improved stability of the test sensor leads to longer shelf-life and use-life of the test sensor.

EXAMPLES

To compare test sensor stability, changes in reagent background as a function of time and temperature and thermal stability, a group of test sensors having an HEC-based reagent was provided as described below in Example 1. Another group of test sensors having a PEO-based reagent was provided as described below in Example 2. The results of the testing are described in Examples 3, 4 and 5 and are depicted in FIGS. 5, 6 and 7a-7d.

Inventive Example 1

HEC-Based Reagent

| REAGENT COMPONENT | WEIGHT %* |
|---|---|
| Purified Water | 60-80 |
| Smectite Clay | 0.2-1.6 |
| Citrate Buffer | 25-200 mMolar |
| Fluorocarbon Surfactant | 0.02-0.1 |
| Hydroxyethyl cellulose | 3.6-6.0 |
| Potassium Ferricyanide | 15-20 |
| Glucose Oxidase Enzyme | 1.0-4.0 |

*Unless other units are indicated.

Comparative Example 2

PEO-Based Reagent

| REAGENT COMPONENT | WEIGHT %* |
|---|---|
| Purified Water | 60-80 |
| Smectite Clay | 0.2-2.2 |
| Citrate Buffer | 25-200 mMolar |
| Fluorocarbon Surfactant | 0.02-0.1 |
| Hydrocarbon Surfactant | 0.2-3.0 |
| Polyethylene Oxide | 3.0-9.0 |
| Potassium Ferricyanide | 15-20 |
| Glucose Oxidase Enzyme | 1.0-4.0 |

*Unless other units are indicated.

Example 3

To assess test sensor stability, a test was performed on two lots of test sensors to determine the percentage of glucose oxidase recovery that occurred after the test sensors were stored at −20 degrees C. and 50 degrees C. for two and four weeks. One lot of test sensors having an HEC-based reagent was compared with a second lot of test sensors having a PEO-based reagent. At the end of the test sensor storage period, the test sensors were extracted with a buffer and the glucose oxidase activity in the test sensor extracts was analyzed using standard enzyme activity analysis methods.

Figure 5:
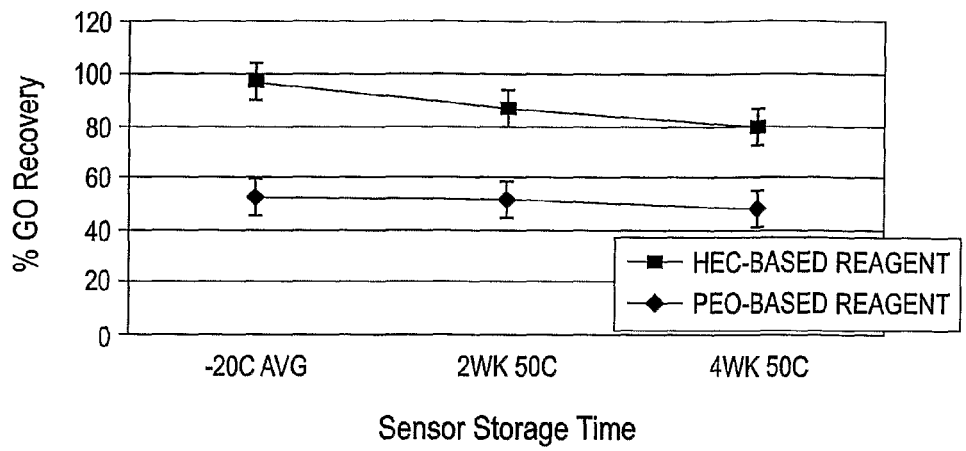
FIG. 5 is graph comparing the percentages of glucose oxidase recovery for test sensors having an HEC-based reagent and a PEO-based reagent according to one embodiment of the present invention.

The results of the testing are shown in FIG. 5. Although both lots of test sensors were formulated with the same amount of glucose oxidase in the reagent, the glucose oxidase activity recovery for the HEC-based reagent was greater than the glucose oxidase activity recovery for the PEO-based reagent. This was true for both lots of test sensors that were stored at −20 degrees C. and 50 degrees C. for two- and four-week periods. The results from the table indicated that test sensors containing the PEO-based reagent contained more non-reactive glucose oxidase. These results indicated that the glucose oxidase activity was more stable at different temperatures and for extended time periods, in some cases near 100% recovery, for test sensors with reagents that contained HEC. This translated into a more stable test sensor during the shelf-life of the test sensor.

Example 4

Figure 6:
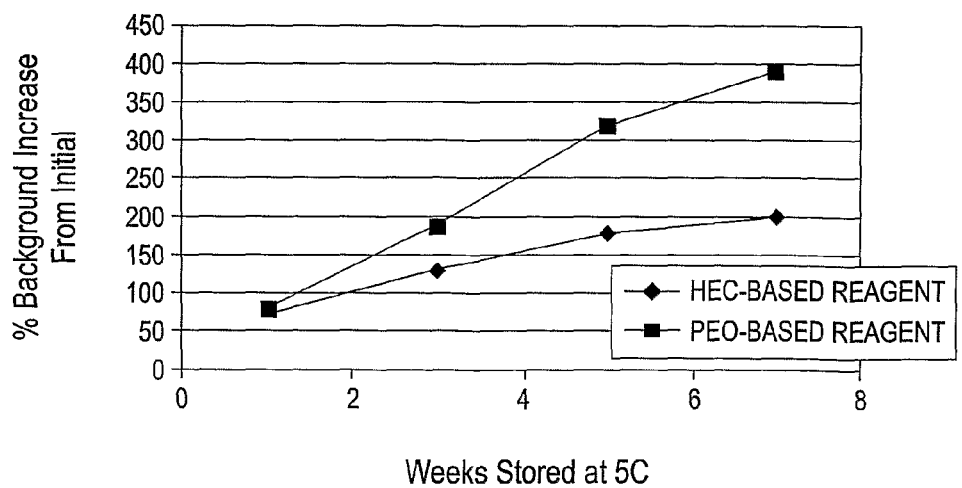
FIG. 6 is a graph comparing the mediator stability as a function of reagent storage time for test sensors having an HEC-based reagent and a PEO-based reagent according to one embodiment of the present invention.
Figure 7A:
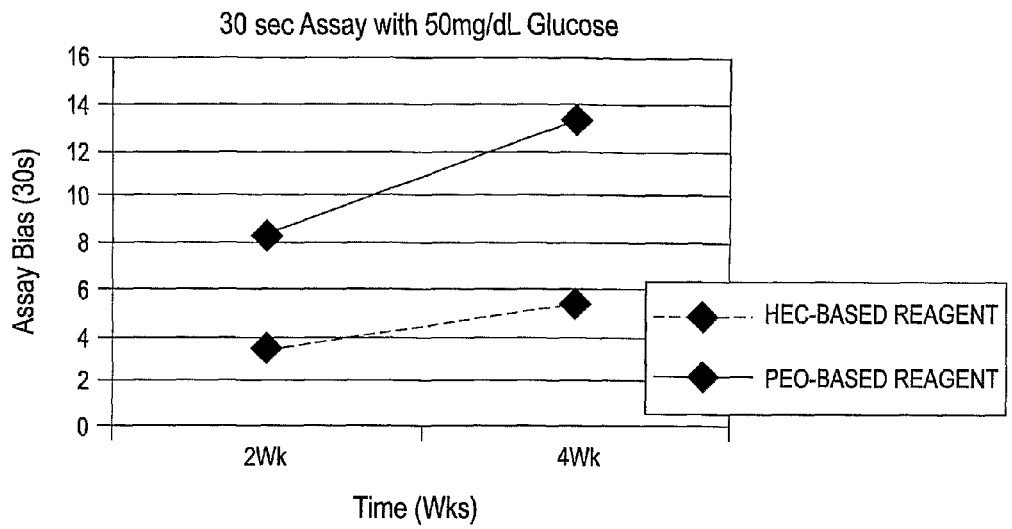
FIGS. 7a-7b and 7c-7d are a series of graphs comparing the assay bias and assay % bias based on 10-second assays and 30-second assays, respectively, for test sensors having an HEC-based reagent and PEO-based reagent according to one embodiment of the present invention.
Figure 7B:
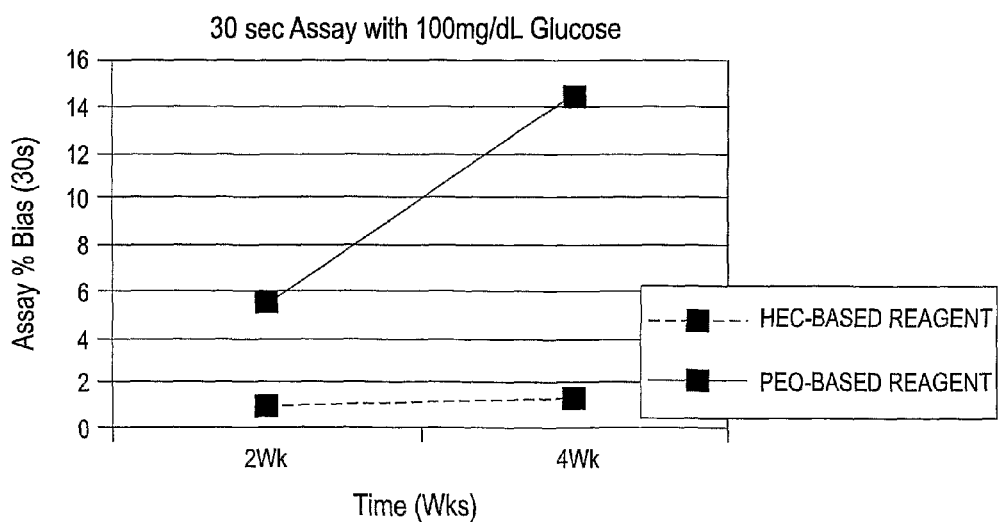
Figure 7C:
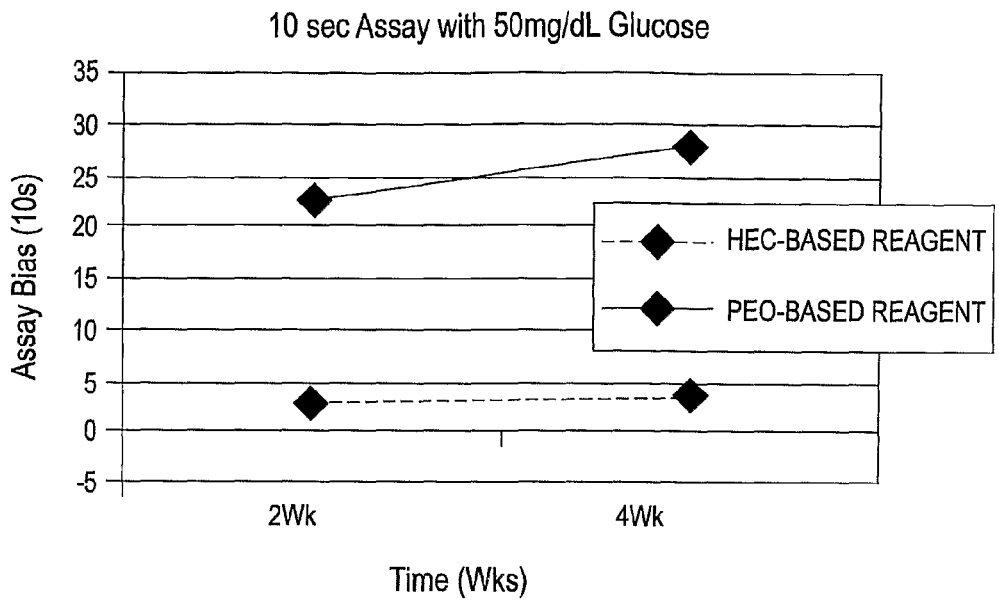
Figure 7D:
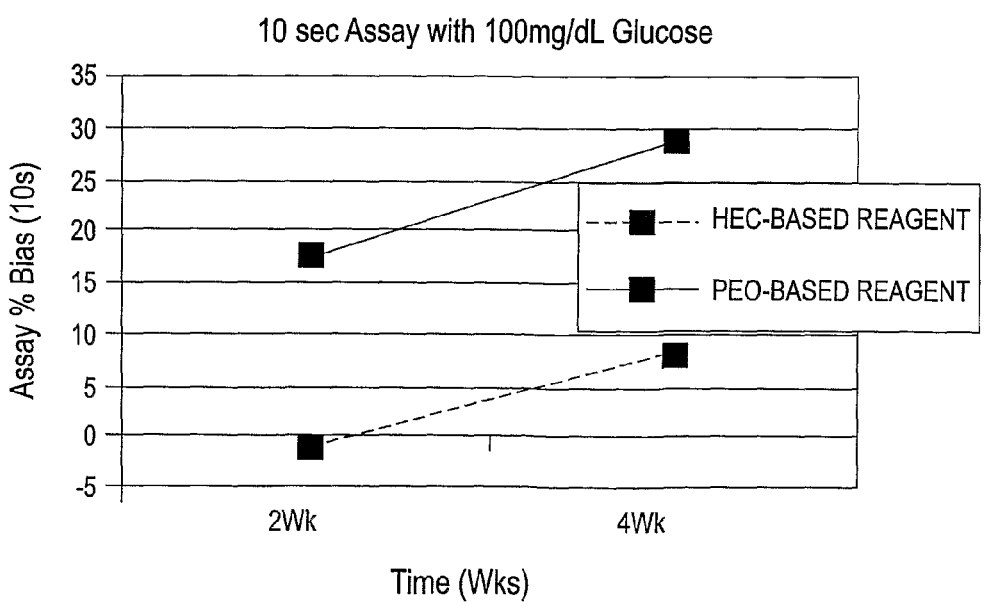

FIG. 6 illustrates the results of testing to assess the reagent background change in test sensors having a HEC-based reagent and in test sensors having a PEO-based reagent as a function of reagent storage time at 5 degrees C. for up to six weeks. The increase in reagent background as a function of reagent storage time is the result of non-glucose related conversion of ferricyanide to ferrocyanide. At each stability checkpoint, the reagent background was analyzed with a flow injection system to quantify the relative amount of ferrocyanide generated during storage. The percent of reagent background increase was calculated by comparing the reagent background current at each checkpoint to the reagent background current at initial checkpoint. As seen in FIG. 6, the HEC-based reagent showed less increase in background over the six week period compared to the PEO-based reagent.

Example 5

FIGS. 7a, 7b, 7c and 7d show a comparison of the assay bias for stressed test sensors formulated with HEC-based and PEO-based reagents. To assess the thermal stability of the test sensors, the test sensors were stored at −20 degrees C. and 50 degrees C. for two and four weeks. At the end of the test sensor storage periods, the test sensors were evaluated with 40% hematocrit whole blood at 50, 100, and 400 mg/dL glucose concentrations. Twenty replicates per samples were collected using 30 second and 10 second assay protocols. The difference in glucose assays results between the 50 degree C. stressed test sensors and the −20 degree C. stressed test sensors was calculated. For samples with 50 mg/dL glucose, the difference in assay results was expressed as "assay bias" (see FIGS. 7a and 7c) and for samples with 100 mg/dL, the difference in assay results was expressed as "assay % bias" (see FIGS. 7b and 7d).

Improvement in stability of the test sensors was most notable at the lower glucose levels due to lower test sensor background drift. The results showed that the differences in the assay bias and assay % bias were more notable when the total assay time was changed from 30 seconds to 10 seconds. The HEC-based reagent dramatically reduced the assay bias between the 50 degree C. and the −20 degree C. test sensors. This was observed for both the 30 second and 10 second assays.

While the test sensor reagent of the present invention has been described for use primarily with an electrochemical test sensor, it is contemplated that the test sensor reagent of the present invention may also be adapted for use with other test sensors, such as optical test sensors.

Alternative Embodiment A

A test sensor reagent composition adapted to assist in determining an analyte concentration of a fluid sample, the reagent comprising an enzyme, an electron transfer mediator, a cellulose polymer and a rheological additive.

Alternative Embodiment B

The composition according to Alternative Embodiment A, wherein the reagent comprises from about 3.6 wt. % to about 6.0 wt. % of the cellulose polymer.

Alternative Embodiment C

The composition according to Alternative Embodiment A, wherein the reagent comprises from about 1 wt. % to about 4 wt. % of the enzyme.

Alternative Embodiment D

The composition according to Alternative Embodiment A, wherein the reagent comprises from about 15 wt. % to about 20 wt. % of the electron transfer mediator.

Alternative Embodiment E

The composition according to Alternative Embodiment A, wherein the reagent comprises from about 0.2 wt. % to about 1.6 wt. % of the Theological additive.

Alternative Embodiment F

The composition according to Alternative Embodiment A, wherein the reagent comprises from about 3.6 wt. % to about 6.0 wt. % of a hydroxyethyl cellulose polymer, from about 1 wt. % to about 4 wt. % of a glucose oxidase enzyme, from about 15 wt. % to about 20 wt. % of a ferricyanide mediator and from about 0.2 wt. % to about 1.6 wt. % of a smectite clay.

Alternative Embodiment G

The composition according to Alternative Embodiment F, wherein the smectite clay includes bentonite, hectorite, montmorillonite, or a combination thereof.

Alternative Embodiment H

The composition according to Alternative Embodiment A, wherein the reagent further comprises about 10 mMolar to about 500 mMolar of a citrate buffer.

Alternative Embodiment I

The composition according to Alternative Embodiment H, wherein the citrate buffer comprises citric acid, sodium citrate, or a combination thereof.

Alternative Embodiment J

The composition according to Alternative Embodiment A, wherein the reagent further comprises from about 0.02 wt. % to about 0.1 wt. % of a fluorocarbon surfactant.

Alternative Embodiment K

The composition according to Alternative Embodiment A, wherein the reagent further comprises from about 1.0 wt. % to about 3.0 wt. % of a hydrocarbon surfactant.

Alternative Embodiment L

The composition according to Alternative Embodiment A, where a total assay time of a test sensor including the test sensor reagent composition is less than about 35 seconds.

Alternative Process M

A method of determining an analyte concentration of a fluid sample comprising the acts of:
providing an electrochemical test sensor adapted to assist in determining the analyte concentration, the electrochemical test sensor comprising a plurality of electrodes including a counter electrode and a working electrode, a fluid receiving area and a test sensor reagent, the test sensor reagent including a cellulose polymer; and
determining the analyte concentration in an assay time of less than about 35 seconds.

Alternative Embodiment N

The electrochemical test sensor according to Alternative Process M, wherein the cellulose polymer comprises hydroxyethyl cellulose.

Alternative Embodiment O

The electrochemical test sensor according to Alternative Process M, wherein the test sensor reagent further comprises an enzyme, an electron transfer mediator and a rheological additive.

Alternative Embodiment P

The electrochemical test sensor according to Alternative Embodiment O, wherein the electron transfer mediator comprises a ferricyanide mediator.

Alternative Embodiment Q

The electrochemical test sensor according to Alternative Embodiment O, wherein the rheological additive comprises a smectite clay.

Alternative Embodiment R

The electrochemical test sensor according to Alternative Embodiment Q, wherein the smectite clay comprises bentonite, hectorite, montrnorillonite, or combinations thereof.

Alternative Embodiment S

The electrochemical test sensor according to Alternative Embodiment O, wherein the enzyme comprises a glucose oxidase enzyme.

Alternative Embodiment T

The electrochemical test sensor according to Alternative Process M, wherein the total assay time is reduced to less than about 25 seconds.

Alternative Process U

A method of determining an analyte concentration of a fluid sample, the method comprising the acts of:
pricking a finger of a test subject to produce the fluid sample;
placing the fluid sample within a test sensor, the fluid sample having at least one analyte;
contacting the fluid sample with a reagent comprising a cellulose polymer, the cellulose polymer assisting in stabilizing the test sensor;

providing an electrical signal indicative of the analyte in the fluid sample; and determining the analyte using the electrical signal.

Alternative Process V

The method according to Alternative Process U, wherein the analyte concentration is determined in less than about 35 seconds.

Alternative Process W

The method according to Alternative Process U, wherein the reagent comprises hydroxyethyl cellulose.

Alternative Process X

The method according to Alternative Process W, wherein the reagent further comprises a glucose oxidase enzyme, a ferricyanide mediator and a smectite clay.

Alternative Process Y

A method of determining an analyte concentration of a fluid sample, the method comprising the acts of:

pricking a finger of a test subject to produce the fluid sample;

placing the fluid sample within a test sensor, the fluid sample having at least one analyte;

contacting the fluid sample with a reagent comprising a cellulose polymer, the cellulose polymer assisting in stabilizing the test sensor; and determining the analyte concentration of the fluid sample.

Alternative Process Z

The method according to Alternative Process Y, wherein the test sensor is an optical test sensor.

Alternative Process AA

A method of screen printing on a substrate, the method comprising the acts of:

providing a screen that includes a first portion with a photosensitive emulsion and a second portion formed in the absence of a photosensitive emulsion;

supplying a reagent on the screen, the reagent comprising a solvent, a cellulose polymer and an enzyme to assist in determining an analyte concentration of a fluid sample; and contacting the reagent onto the substrate via the second portion of the screen.

Alternative Process BB

The method according to Alternative Process AA, wherein the reagent further comprises a Theological additive.

Alternative Process CC

The method according to Alternative Process BB, wherein the rheological additive is a smectite clay.

Alternative Process DD

The method according to Alternative Process CC, wherein the smectite clay includes hectorite, bentonite, montmorillonite, or combinations thereof.

Alternative Process EE

The method according to Alternative Process BB, wherein the rheological additive is a thixotropic material.

Alternative Process FF

The method according to Alternative Process AA, wherein the reagent further comprises an electron transfer mediator.

While the invention is susceptible to various modifications and alternative forms, specific embodiments thereof have been shown by way of example in the drawings and are described in detail herein. It should be understood, however, that it is not intended to limit the invention to the particular forms disclosed, but, to the contrary, the intention is to cover all modifications, equivalents and alternatives falling within the spirit and scope of the invention as defined by the appended claims.

The invention claimed is:

1. A test sensor reagent composition adapted to assist in determining an analyte concentration of a fluid sample, the reagent comprising an enzyme, an electron transfer mediator, a cellulose polymer and a rheological additive, wherein the rheological additive is smectite clay, wherein the test sensor reagent composition comprises from about 3.6 wt. % to about 6.0 wt. % of a hydroxyethyl cellulose polymer, from about 1 wt. % to about 4 wt. % of a glucose oxidase enzyme, from about 15 wt. % to about 20 wt. % of a ferricyanide mediator and from about 0.2 wt. % to about 1.6 wt. % of the smectite clay.

2. The composition according to claim 1, wherein the cellulose polymer, rheological additive and the enzyme are present in a single layer.

3. The composition according to claim 1, wherein the reagent further comprises about 10 mMolar to about 500 mMolar of a citrate buffer.

4. A method of determining an analyte concentration of a fluid sample comprising the acts of:

providing an electrochemical test sensor adapted to assist in determining the analyte concentration, the electrochemical test sensor comprising a plurality of electrodes including a first electrode and a second electrode, a fluid receiving area and a test sensor reagent, the test sensor reagent composition comprising a cellulose polymer, a rheological additive, and an enzyme, the rheological additive is smectite clay, wherein the test sensor reagent composition comprises from about 3.6 wt. % to about 6.0 wt. % of a hydroxyethyl cellulose polymer, from about 1 wt. % to about 4 wt. % of a glucose oxidase enzyme, from about 15 wt. % to about 20 wt. % of a ferricyanide mediator and from about 0.2 wt. % to about 1.6 wt. % of the smectite clay; and determining the analyte concentration in an assay time of less than about 35 seconds.

5. The method according to claim 4, wherein the cellulose polymer, rheological additive and the enzyme are present in a single layer.

6. The method according to claim 4, wherein the total assay time is reduced to less than about 25 seconds.

7. A method of determining an analyte concentration of a fluid sample, the method comprising the acts of:

providing a fluid sample;

contacting a test sensor with the fluid sample, the fluid sample having at least one analyte;

contacting the fluid sample with a reagent composition comprising a cellulose polymer, a rheological additive and an enzyme, the rheological additive is smectite clay, wherein the test sensor reagent composition comprises from about 3.6 wt. % to about 6.0 wt. % of a hydroxyethyl cellulose polymer, from about 1 wt. % to about 4 wt. % of a glucose oxidase enzyme, from about 15 wt. % to about 20 wt. % of a ferricyanide mediator and from about 0.2 wt. % to about 1.6 wt. % of the smectite clay;
providing an electrical signal indicative of the analyte in the fluid sample; and
determining the analyte using the electrical signal.

8. The method according to claim 7, wherein the analyte concentration is determined in less than about 35 seconds.

9. A method of determining an analyte concentration of a fluid sample, the method comprising the acts of:
providing the fluid sample;
contacting a test sensor with the fluid sample, the fluid sample having at least one analyte;
contacting the fluid sample with a reagent composition comprising a cellulose polymer, a rheological additive and an enzyme, the rheological additive is smectite clay, wherein the test sensor reagent composition comprises from about 1 wt. % to about 10 wt. % of a hydroxyethyl cellulose polymer, from about 0.5 wt. % to about 5 wt. % of a glucose oxidase enzyme, from about 1 wt. % to about 20 wt. % of a ferricyanide mediator and from about 0.2 wt. % to about 3 wt. % of the smectite clay; and
determining the analyte concentration of the fluid sample.

10. The method according to claim 9, wherein the test sensor is an optical test sensor.

11. A test sensor reagent composition adapted to assist in determining an analyte concentration of a fluid sample, the reagent comprising an enzyme, an electron transfer mediator, a cellulose polymer and a rheological additive, wherein the cellulose polymer, the rheological additive and the enzyme are present in a single layer, and wherein the rheological additive is a smectite clay, wherein the test sensor reagent composition comprises from about 1 wt. % to about 10 wt. % of a hydroxyethyl cellulose polymer, from about 0.5 wt. % to about 5 wt. % of a glucose oxidase enzyme, from about 1 wt. % to about 20 wt. % of a ferricyanide mediator and from about 0.2 wt. % to about 3 wt. % of the smectite clay, wherein the hydroxyethyl cellulose polymer has a molecular weight from about 25,000 to about 2,000,000.

12. The composition according to claim 11, wherein the reagent composition comprises from about 0.2 wt. % to about 1.6 wt. % of the smectite clay.

13. A test sensor reagent composition adapted to assist in determining an analyte concentration of a fluid sample, the reagent comprising an enzyme, an electron transfer mediator, a cellulose polymer and a rheological additive, wherein the test sensor reagent composition comprises from about 1 wt. % to about 10 wt. % of a hydroxyethyl cellulose polymer, from about 0.5 wt. % to about 5 wt. % of a glucose oxidase enzyme, from about 1 wt. % to about 20 wt. % of a ferricyanide mediator and from about 0.2 wt. % to about 3 wt. % of the rheological additive, wherein the hydroxyethyl cellulose polymer has a molecular weight from about 25,000 to about 2,000,000.

14. The composition according to claim 13 wherein the reagent composition comprises from about 0.2 wt. % to about 1.6 wt. % of the rheological additive.

15. The composition according to claim 13 wherein the cellulose polymer, the rheological additive and the enzyme are present in a single layer.

* * * * *

UNITED STATES PATENT AND TRADEMARK OFFICE
CERTIFICATE OF CORRECTION

PATENT NO. : 8,940,153 B2
APPLICATION NO. : 12/083952
DATED : January 27, 2015
INVENTOR(S) : Amy H. Chu, Andrew J. Edelbrock and Hope G. Spradlin It is certified that error appears in the above-identified patent and that said Letters Patent is hereby corrected as shown below:

ON THE TITLE PAGE

On Page 2, item 56, under "OTHER PUBLICATIONS", in Column 2, Line 10, delete "membrance" and insert -- membrane --, therefor.

IN THE SPECIFICATION

In Column 2, Line 60, delete "is" and insert -- is a --, therefor.
In Column 4, Line 57, delete "Theological" and insert -- rheological --, therefor.
In Column 5, Line 37, delete "xanthum" and insert -- xanthan --, therefor.
In Column 9, Line 22, delete "Theological" and insert -- rheological --, therefor.
In Column 10, Line 43, delete "montrnorillonite," and insert -- montmorillonite, --, therefor.
In Column 11, Line 56, delete "Theological" and insert -- rheological --, therefor.

Signed and Sealed this
Sixteenth Day of February, 2016

Michelle K. Lee
*Director of the United States Patent and Trademark Office*